(12) United States Patent
Göbel et al.

(10) Patent No.: US 6,918,916 B2
(45) Date of Patent: Jul. 19, 2005

(54) TARGET APPARATUS

(75) Inventors: Jürgen Göbel, Östringen (DE);
Eberhard Körner, Bretten (DE);
Helmut Heckele, Knittlingen (DE)

(73) Assignee: Richard Wolf GmbH, Knittlingen (DE)

( * ) Notice: Subject to any disclaimer, the term of this patent is extended or adjusted under 35 U.S.C. 154(b) by 261 days.

(21) Appl. No.: 10/247,975

(22) Filed: Sep. 20, 2002

(65) Prior Publication Data

US 2003/0051591 A1 Mar. 20, 2003

(30) Foreign Application Priority Data

Sep. 20, 2001 (DE) .......................................... 101 46 452

(51) Int. Cl.$^7$ .............................................. A61B 17/58
(52) U.S. Cl. ........................................................ 606/96
(58) Field of Search ............................... 606/53, 79, 80, 606/86, 87, 96, 97, 98, 102, 103, 104, 167, 168, 170, 171, 182

(56) References Cited

U.S. PATENT DOCUMENTS

| 4,672,957 A | 6/1987 | Hourahane ............. 128/92 VD |
| 5,154,720 A | 10/1992 | Trott et al. .................... 606/96 |
| 5,350,383 A | 9/1994 | Schmieding et al. .......... 606/96 |
| 5,458,602 A * | 10/1995 | Goble et al. ................... 606/96 |
| 5,562,664 A * | 10/1996 | Durlacher et al. ............. 606/96 |
| 5,667,509 A * | 9/1997 | Westin .......................... 606/80 |
| 5,688,284 A * | 11/1997 | Chervitz et al. .............. 606/96 |
| 5,891,150 A | 4/1999 | Chan ............................. 606/96 |
| 5,968,050 A | 10/1999 | Torrie ............................ 606/87 |
| 6,120,511 A | 9/2000 | Chan ............................. 606/96 |
| 6,254,606 B1 * | 7/2001 | Carney et al. ............... 606/102 |

FOREIGN PATENT DOCUMENTS

EP 0 797 955 A1 10/1997 ........... A61B/17/17

* cited by examiner

Primary Examiner—Eduardo C. Robert
Assistant Examiner—Anuradha Ramana
(74) Attorney, Agent, or Firm—Cohen, Pontani, Lieberman & Pavane

(57) ABSTRACT

The target apparatus for positioning a drilling tool with respect to a drilling channel to be created in a bone consists of a target hook and a guide arm which is releasably connected to this and on which there is arranged a receiver for the drilling tool, and a guide path in the form of a laterally through-going open groove for the guide arm. The guide arm may be displaced and fixed in the guide path. A simple assembly and disassembly of the apparatus is achieved in that the guide arm on the side of the apparatus is applied into the guide path through the groove opening and reversely, by lifting away out of the groove, may be separated from the target hook.

14 Claims, 3 Drawing Sheets

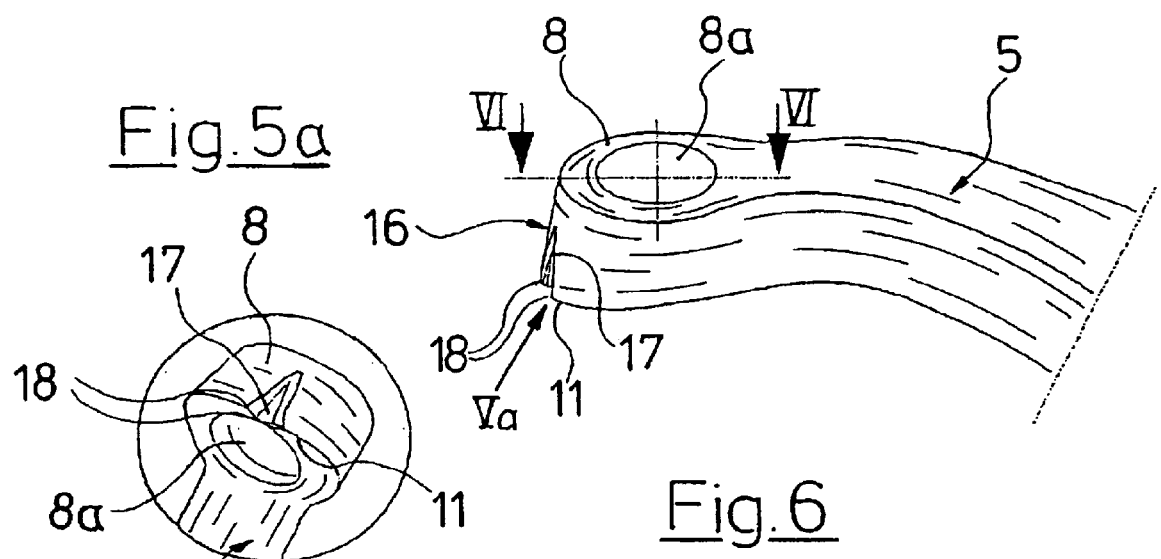
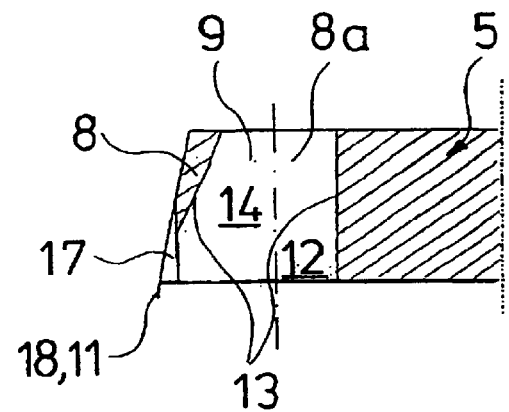

TARGET APPARATUS

BACKGROUND OF THE INVENTION

The invention relates to a target apparatus for positioning a drilling tool with respect to a drill channel to be created, consisting of a target hook and a guide arm releasably fastened to this, on which there is arranged a receiver for the drilling tool and on which there is formed a guide path in the form of a laterally through-going open groove for the guide arm which is displaceable and fixable in the guide path.

Such target apparatus are applied for reconstruction for example of a ligament in the knee joint which has torn for example on account of an accident. In particular, for the replacement of the front cruciate ligament with the quadriceps tendon by way of an arthroscopic operation there exists the possibility of an implant-free anchorage of a part of the quadriceps tendon. Within the framework of this operation it is required to obtain a spongy bone cylinder from the tibia with which the defect filling at the patella and the additional transplant blockage in the tibia may be carried out. For this a drill channel must firstly be placed in the tibia and the femur in an exact manner.

For an exact as possible placing of drill channels one uses target apparatus of the previously mentioned type. Such a target apparatus is known from U.S. Pat. No. 5,968,050. This comprises a guide arm on which the drilling tool may be attached via a suitable receiver. For aligning the drilling tool a target hook is connected to the guide arm, which may be aligned at a previously set angle to the guide arm. The target hook at its distal region has an arcuate shape with a sharp tip which serves for anchoring the end of the target hook on the bone during the drilling procedure, so that the target apparatus may not slip away. Similar designs are known from U.S. Pat. Nos. 4,672,957, 5,154,720 and 5,350,383 and from EP 0 797 955 A1.

A disadvantage of these target apparatus lies in the fact that the arcuate target hook to be introduced into the joint cavity may create injuries on account of the sharp tip. Although this risk may be kept small with the correct handling of the apparatus and with a careful execution of the endoscopic operation, it may never be completely ruled out.

On account of the arcuate shape of the target hook there further arises the disadvantage that an exact positioning of the bore to be incorporated into the bone is not possible on account of the constantly present mismatch between the tip of the target hook and the through bore for the required guide wire and the drill, which is located at a distance to this tip.

Finally with known target apparatus it is also disadvantageous that on account of design and an account of the anatomical conditions, after an effected incorporation of the bore it is very difficult to be able to be removed again out of the cavity of the joint, not least because a prior separation of the guide arm from the target hook is not possible due to the restricted space conditions. There therefore exists the danger that injuries may occur also in this phase of the operation.

BRIEF SUMMARY OF THE INVENTION

It is the object of the invention to improve a target apparatus of the described type such that one rules out the danger of the occurrence of undesired injuries of the joint cavity, and specifically when incorporating and applying the end of the target hook in the joint cavity or on the bone as well as on removal of the target hook from the joint cavity. Furthermore it is to be possible to exactly position the target apparatus so that the bore may be incorporated into the bone with high precision. In particular it is to be possible to place the tibia insertion point as exactly as possible in the case of the reconstruction of a cruciate ligament.

Proceeding from a target apparatus of the known type, this object is achieved in that the guide arm may be applied through the groove opening into the guide path from one side of the apparatus. By way of this one achieves the particular advantage that the target hook and the guide arm may be separated again from one another simply by way of a lateral displacement of both parts without it being necessary, as with existing target apparatus, of having to slide the guide arm out of the guide path or groove. For connecting the target hook to the guide arm the same is also the case in reverse, since the guide arm quasi as an insert needs only to be applied into the guide path from the side and then fastened in the suitable position. The assembly and disassembly of the target apparatus becomes particularly favourable and simple if the cross sections of the groove and of the guide arm are in each case complementarily rectangular.

On the target hook there is provided a blocking toggle with a tensioning eccentric with which the guide arm may be fastened in the guide path or groove by clamping, and specifically by rotating the blocking toggle in one direction. By rotating the blocking toggle in the opposite direction one may again release the non-positive connection again and the guide arm may be lifted simply from the target hook out of its guide path.

The distal free end of the target hook is formed by an annular through part with a through opening for the drilling tool, wherein the axes for the receiver of the drilling tool and the through opening are aligned. Furthermore at the distal end of the target hook there is provided a cutter directed proximally towards the receiver as a replacement for the tip which otherwise is usually sharp. This cutter is usefully provided at the proximal end of the through bore which is directed towards the receiver.

In order to be able to easily introduce the guide wire for the drilling tool and the drilling tool itself into and through the through opening and to be able finally to lead the drilling tool axially in the through opening in a perfect manner, this through opening in a first distal section has a cylindrical contour to which there joins a proximally extending truncated cone shaped contour in a second section so that the guide wire may be easily introduced into the first section and finally the drilling tool in the distal section.

Not only is an atraumatic and thus gentle positioning of the end region of the target hook in the passage cavity possible with the target apparatus according to the invention, but also the simple removal of the target hook from this region, after the guide arm and target hook as described have previously been separated from one another so that the operator when removing the target hook is not hindered by the guide arm, and the target hook may be removed from the joint cavity in a controlled manner. Furthermore a precise placing of the bore may be effected since the end region of the target hook bears on the insertion location at a small radial and axial distance. In particular therefore it is achieved that by way of this, after the target bore has been set, it is possible for the target hook to be able to be removed on the spot independently of the removed guide arm.

BRIEF DESCRIPTION OF THE DRAWINGS

In the drawings, wherein like reference characters denote similar elements throughout the several views:

FIG. 5 is a perspective view of the distal end of the target hook of FIG. 2;

FIG. 5a is a detailed view of the end of the distal end of the target hook along the line Va in FIG. 5; and FIG. 6 is a sectional view of the target hook along line VI—VI of FIG. 5.

DETAILED DESCRIPTION OF THE INVENTION

Figure 1:
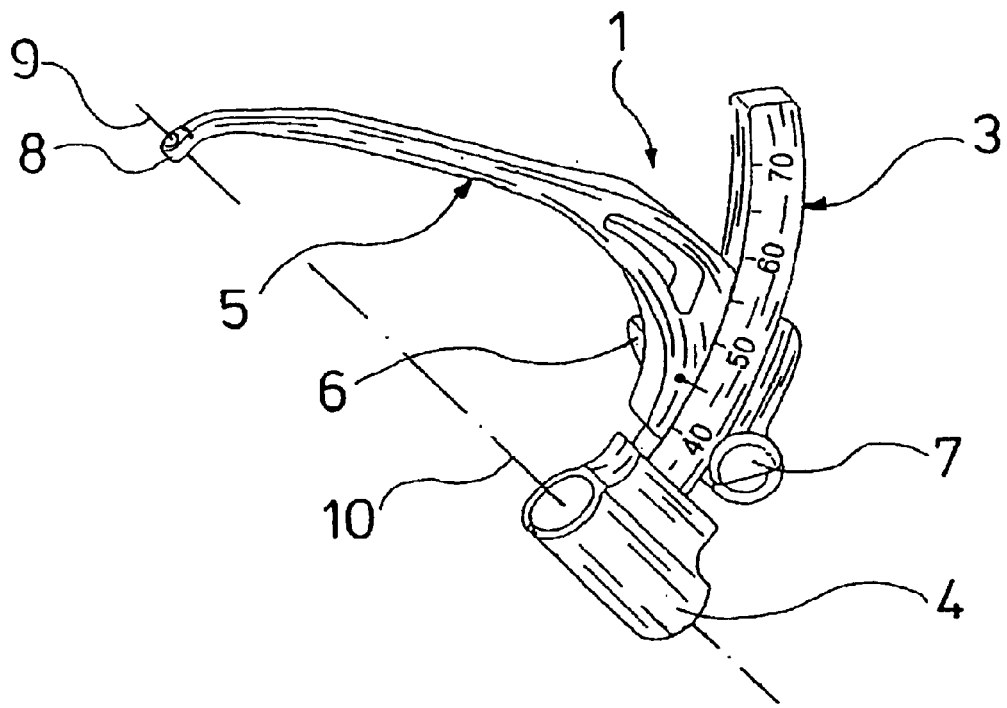
FIG. 1 is a perspective view of a target apparatus according to an embodiment of the present invention with out an applied drilling tool.
Figure 3:
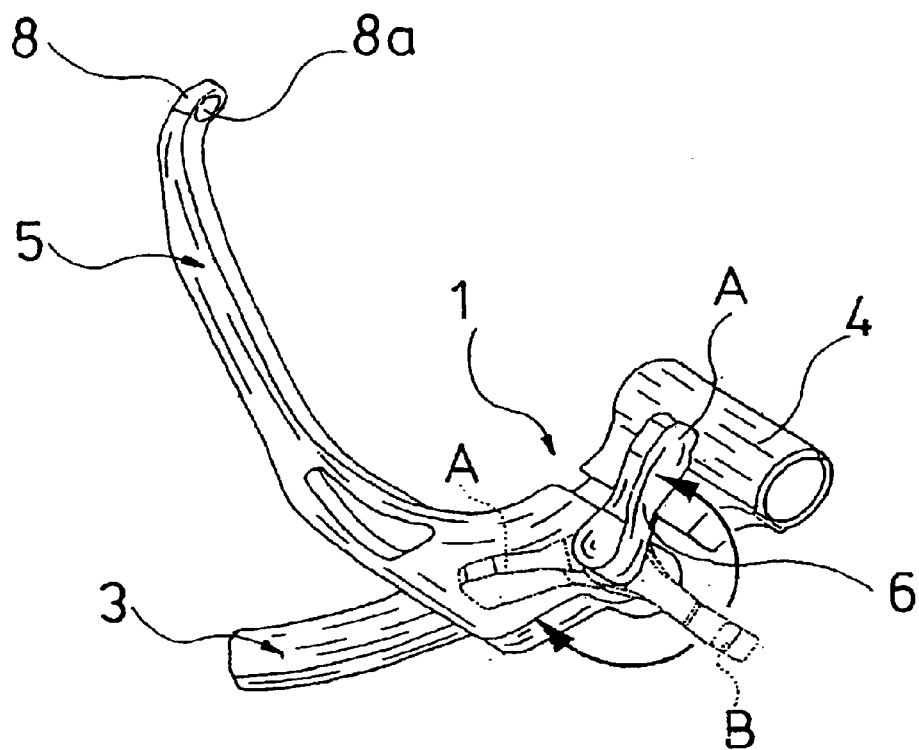
FIG. 3 is a perspective view showing the target apparatus of FIG. 1 pivoted by 180 degrees relative to the position shown in FIG. 1.
Figure 4:
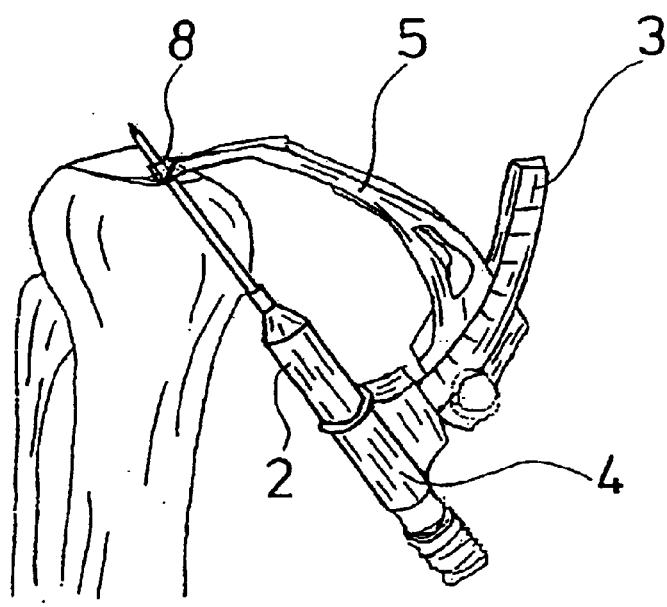
FIG. 4 is a perspective of the target apparatus of FIG. 1 with an applied drilling tool in a position aligned with a bone to be machined.

In the FIGS. 1, 3 and 4 there is to be seen a target apparatus 1 which includes a guide arm 3 and a target hook 5 fastened thereto. The guide arm 3 has a receiver 4 which has a hollow-cylindrical shape and into which the housing of a drilling tool 2 (see FIG. 4) may be applied.

The drilling tool 2 during the incorporation of a bore into a bone (FIG. 4) is adjusted axially in the direction of the bone. For this, but not shown, on the cylindrical housing of the drilling tool 2 at least over a part of the circumference, preferably over half the circumference, there is arranged a toothing which cooperates with a pawl arranged in the receiver. The pawl is biased with a compression spring. With this the drilling tool may be displaced distally in the receiver 4 in steps, wherein a return action of the tool is prevented in that the toothing comprises perpendicular flanks in the return direction on which the pawl comes to bear in a blocking manner. Thus on operation of the drilling tool only an axial displacement of the drill in the direction of the distal end of the target hook is possible, but not in the proximal direction. For removing the drilling tool the described blocking mechanism may be deactivated by hand so that the drilling tool together with the drill may be taken away from the target apparatus.

The guide arm 3 of the target apparatus is formed arc-shaped and has an angular scale which indicates at which angle the target hook 5 is set to the axis 10 of the drilling tool 2. A complementary, arc-shaped guide path 27 in the form of a groove (FIG. 2) is machined into the target hook 5 corresponding to the shape of the arc of the guide arm 3. At one end of the guide path 27 there is arranged a tensioning eccentric 7 which may be adjusted via a rotatable blocking toggle 6.

Figure 2:
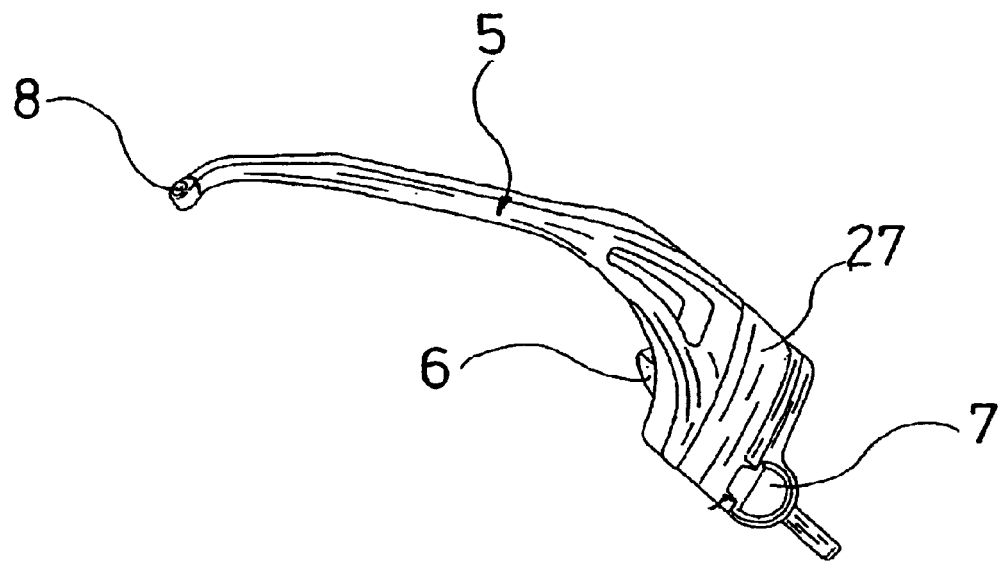
FIG. 2 is a perspective view of a target hook of the target apparatus of FIG. 1.

If the tensioning eccentric 7 is located in the position shown in FIG. 2, the target hook 5 may be displaced on the guide arm 3 and simply lifted from this by hand. If the blocking toggle 6 is pivoted about a certain angle, the target hook 5 is then fixed on account of the force of the guide path 27 exerted by the tensioning eccentric 7 on the guide arm 3.

For this the blocking toggle 6 may be selectively rotated in the clockwise direction or in the other direction, as is to be seen in FIG. 3. In FIG. 3 the blocking toggle 6 is shown in unbroken lines in a position A in which the guide arm 3 and target hook 5 are rigidly connected to one another with a non-positive fit. In the clamping position A the blocking toggle 6 according to FIG. 3 lies such that during the operation any inadvertent rotation of the blocking toggle 6 is not possible. The position of the blocking toggle 6 in which the target hook 5 may be removed from the guide arm by lifting away is indicated at B in FIG. 3. In FIG. 4 it is to be seen how the distal-side end of the target hook 5 bears on the surface of the bone with a cutter which is yet to be described.

For the precise fixing of the bore channel 2 to be incorporated into the bone by way of a drilling tool, the target hook 5 at its distal end comprises an annular or cylindrical through part 8 which is formed in the end of the target hook 5. The through part 8 which externally over half the circumference essentially has the shape of a cylinder—over the remaining circumference it is integrally connected to the end of the target hook 5—has a through opening 8a for the drilling tool with an axis 9 which is aligned to the axis 10 of the drilling tool 2 (FIG. 1).

Details of the design of the distal end of the target hook are to be deduced from the FIGS. 5, 5a, and 6. While the outer contour of the passage part 8 is largely cylindrical, the inner passage of this part consists of a half truncated cone shaped section 14 and a half cylindrical section 12, whose outer surfaces 13 blend into one another in a flowing manner.

In the distal free end of the target hook 5 there is provided a cutter 11 which is directed proximally towards he receiver 4 and which is formed at the proximal end of the through part 8 (FIG. 6). This cutter serves for the secure bearing of the distal end of the target hook on the bone. From FIG. 6 it is evident that the free and effective section of the cutter only runs on a part of a circle.

In order to effectively prevent a sliding of the cutter 11 or cutting edge away from the bone, the cutter is divided by a recess 17 which for example is V-shaped, by which means there arise two hook-shaped sharp edges 18 arranged at a small distance to one another.

In comparison to known designs of the distal end of the target hook with a hook tip, it results that with the design according to the invention there is only a small radial distance between the bearing point of the cutter 11 on the bone and the axis 10 of the drilling tool 2. This renders possible a considerably more exact positioning of the bore than with conventional target apparatus.

The shape of the end region 16 of the annular part 8 with the cutter 11 permits a hooking of the distal end of the target hook 5 directly on the tibal insertion, e.g. the front cruciate ligament. By way of the annular, externally rounded through part 8 at the distal end of the target hook 5 there results the advantage that the target hook may be introduced into the knee joint and again removed from this in an atraumatic manner without at the same time injuries to the tissue occurring on account of the cutter.

What is claimed is:

1. A target apparatus for positioning a drilling tool relative to a drill channel to be created, comprising:
   a guide arm having a receiver for receiving the drilling tool; and
   a target hook having a guide path with a longitudinal length and two ends, said guide path being defined in said target hook by a through-going laterally open groove, such that the ends and one lateral side of said guide path are open, wherein said guide arm is releasably fastened to said target hook in said guide path, said guide arm being selectively displaceable along the length of said guide path and fixable in said guide path, and said guide arm being laterally insertable into and removable from the guide path through the open lateral side of the guide path.

2. The target apparatus of claim 1, wherein said guide path and said guide arm comprise complementary cross sections.

3. The target apparatus of claim 1, further comprising a blocking toggle connected to said target hook and a tensioning eccentric connected to said blocking toggle, said tensioning eccentric being actuatable by said blocking toggle for selectively fixing said guide arm relative to said target hook by tensioning said guide arm in said guide path.

4. The target apparatus of claim 1, wherein said target hook comprises a proximal end proximate said guide path and a distal end having an annular through part defining a through opening for receiving a drilling portion of the drilling tool, and wherein an axis of said through opening is aligned with an axis of said receiver.

5. The target apparatus of claim 4, further comprising a cutter arranged proximate said distal end of said target hook, said cutter facing said receiver.

6. The target apparatus of claim 5, wherein said through opening includes a first section having a cylindrical contour and a second section having a proximally extending truncated cone-shaped contour, said second section joining said first section.

7. The target apparatus of claim 6, wherein said cutter is arranged on a proximal end of said annular through part.

8. The target apparatus of claim 7, wherein said cutter includes a recess defined between two hook-shaped sharp edges arranged at a distance from each other.

9. The target apparatus of claim 6, wherein said cutter includes a recess defined between two hook-shaped sharp edges arranged at a distance from each other.

10. The target apparatus of claim 5, wherein said cutter is arranged on a proximal end of said annular through part.

11. The target apparatus of claim 10, wherein said cutter includes a recess defined between two hook-shaped sharp edges arranged at a distance from each other.

12. The target apparatus of claim 5, wherein said cutter includes a recess defined between two hook-shaped sharp edges arranged at a distance from each other.

13. The target apparatus of claim 4, wherein said through opening includes a first section having a cylindrical contour and a second section having a proximally extending truncated cone-shaped contour, said second section joining said first section.

14. The target apparatus of claim 1, wherein said target hook comprises a proximal end proximate said guide path and a distal end, a cutter arranged proximate said distal end of said target hook facing said receiver.

* * * * *